Figure 1:
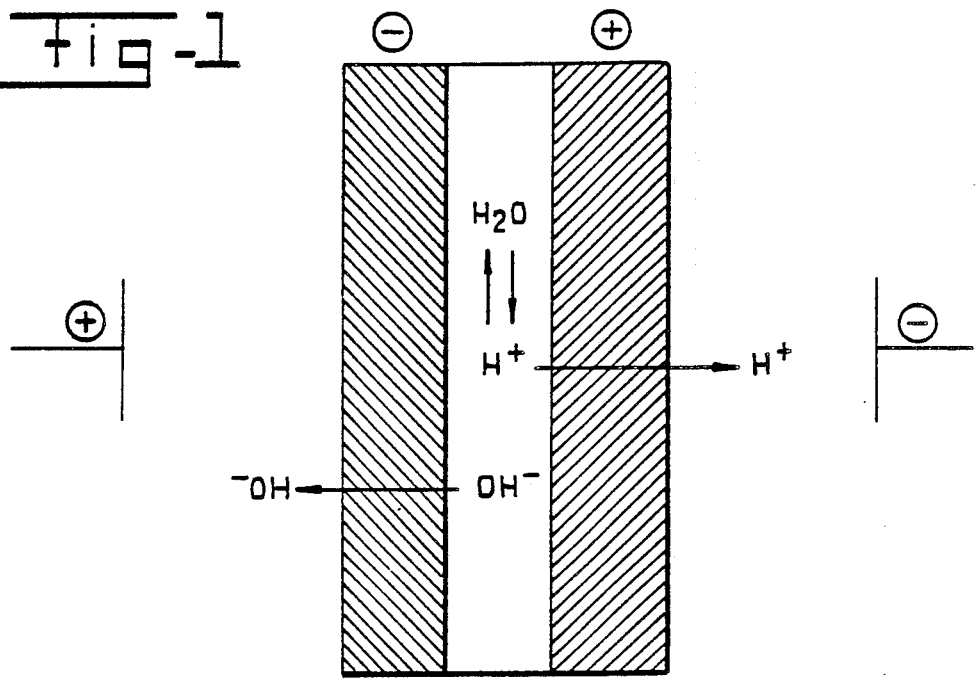

United States Patent [19]
Van Nispen et al.

[11] Patent Number: 5,002,881
[45] Date of Patent: Mar. 26, 1991

[54] PROCESS FOR THE FERMENTATIVE PREPARATION OF ORGANIC ACIDS

[75] Inventors: Joannes G. M. Van Nispen, Bergen op Zoom; Ronald Jonker, The Hague, both of Netherlands

[73] Assignee: Cooperatieve Vereniging Suiker Unie U.A., Breda, Netherlands

[21] Appl. No.: 365,842

[22] Filed: Jun. 13, 1989

[30] Foreign Application Priority Data

Jun. 14, 1988 [NL] Netherlands ........................ 8801516

[51] Int. Cl.$^5$ ........................ C12R 1/07; C12R 1/225; C12R 1/245; C12P 7/56

[52] U.S. Cl. ................................. 435/139; 435/832; 435/856

[58] Field of Search ............... 435/139, 832, 856

[56] References Cited

PUBLICATIONS

Derwent ABS 82-69082e/33 (J57110192) Mitsubishi Chem 7-1982.
Derwent ABS 83-36182k/15 (J58040093) 3-1983, Nakayama.
Derwent ABS 87-207413/30 (EP230021) 7-1987, Czytko.

*Primary Examiner*—Herbert J. Lilling
*Attorney, Agent, or Firm*—Webb, Burden, Ziesenheim & Webb

[57] ABSTRACT

The present invention relates to a process for the fermentative preparation of lactic acid, by allowing a sterilized growth medium to be continuously fermented in a reaction vessel by a culture of bacilli of the genus Bacillus, which form lactic acid, keeping the pH of the reaction mixture at 3 to 9 with an aqueous solution of XOH (where X is $NH_4$ or a metal whose hydroxide and whose salt of lactic acid are watersoluble), subjecting the fermented reaction mixture to an ultrafiltration, recycling the retentate to the reaction vessel, and concentrating the permeate and subsequently subjecting it to an electrodialysis wherein bipolar membranes are used, in which process the lactate is decomposed into the lactic acid and XOH.

2 Claims, 2 Drawing Sheets

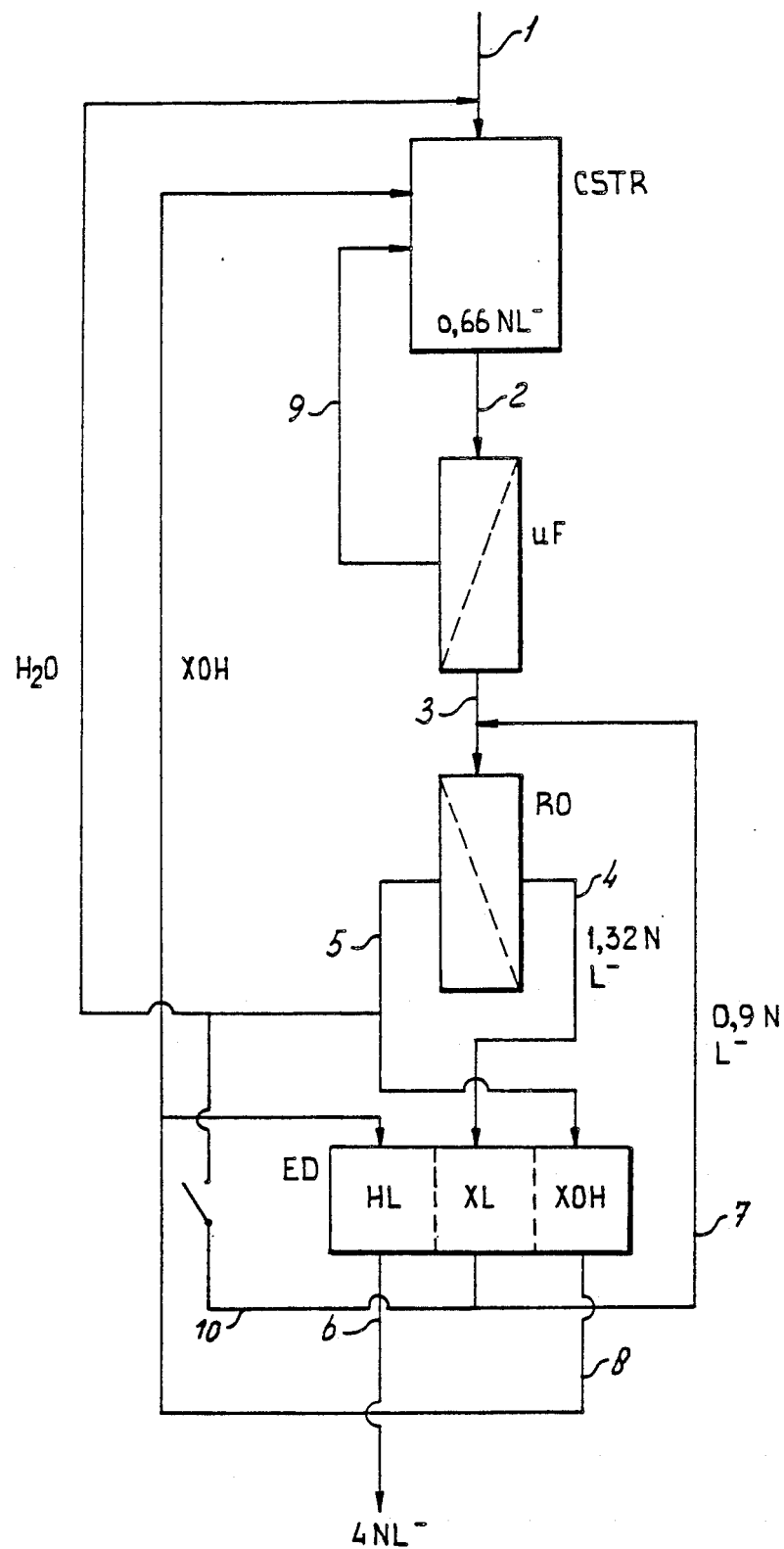

PROCESS FOR THE FERMENTATIVE PREPARATION OF ORGANIC ACIDS

The invention relates to a process for the fermentative preparation of lactic acid, by allowing a sterilized growth medium to be continuously fermented in a reaction vessel by a culture of bacteria which form lactic acid, keeping the pH of the reaction mixture at 3 to 9 with an aqueous solution of XOH (where X is $NH_4$ or a metal whose hydroxide and whose salt of lactic acid are water-soluble), subjecting the fermented reaction mixture to an ultrafiltration, recycling the retentate to the reaction vessel, and concentrating the permeate by subjecting it in a two- or three compartment cell to an electrodialysis wherein bipolar membranes are used, in which process the salt formed is decomposed into the lactic acid and XOH, where XOH has the above mentioned meaning.

In Chem. Ing. Tech., 59, 952–954 (1987) a process is disclosed for continuously fermenting glucose to prepare lactic acid in a fermentation apparatus and extracting the lactic acid formed by using electrodialysis. In this known procedure, a strain of *Lactobacillus casei* is used as a lactic acid-forming microorganism which ferments glucose to form lactic acid in a concentrated aqueous glucose solution in the presence of yeast extract and inorganic salts. The fermentation medium is recycled through an electrodialysis apparatus. The current level in the electrodialysis apparatus is controlled by measuring the pH in the fermenter (see European Patent Application 230,021, column 3, lines 31-33: "Der Fermentor (2) kann mit einer pH-Elektrode ausgerüstet sein, durch die die Stromstärke in der Elektrodialyse-Einheit (4) gesteuert wird"). As a result of this, it is possible to remove the lactic acid formed at the same rate from the fermentation liquid as that at which it is formed in the fermenter. It is remarkable that even without special measures, the system is not contaminated with foreign microorganisms; it appears to be possible, however, to attribute this to the fact that the electrodialysis system selectively inactivates contaminating microorganisms because their growth rate is low in comparison with that of the lactic acid-forming microorganisms.

As disadvantages of this known system, mention is made of the loss of approximately 7% of the lactic acid produced by diffusion through the cation-exchanging membrane into the sulphuric acid solution of the anode recirculation. A portion of said lactic acid is oxidized to pyruvic acid and diffuses towards the acid compartment so that the product flow contains approx. 5.2 mg of pyruvic acid per gram of lactic acid.

Another disadvantage is related to the increase in the electrical resistance as a consequence of the adherence of bacteria to the membrane which may be that high after 30-100 h that the preparation has to be interrupted. This disadvantage can be solved by microfiltration of the fermentation liquid, in which process the retentate containing the biomass is recycled to the fermenter while the permeate is electrodialyzed.

An attempt had already been made earlier to carry out the purely fermentative part of the lactic acid preparation continuously by E. Ohleyer, H. W. Blanch and C. R. Wilke, "Continuous production of lactic acid in a cell recycle reactor", Applied Biochem. Biotechnol. 11, 317-332 (1985) on a laboratory scale. In this improved method, the pH of the fermentation liquid is held at the required value with $NH_4OH$. Since ammonium lactate is soluble in water, the fermentation medium can be subjected to an ultrafiltration, in which process the retentate containing the biomass can be recycled again to the reaction vessel while the permeate is obtained directly. By proceeding in this manner, the volume of the reaction vessel requires only to be small because the volumetric production rate which can be achieved with a cell recycling is large. Said high rate is a consequence of the high biomass concentration in the reaction vessel and the large throughput rate of the medium.

Further Chem. Ing. Tech. 61, 428-429 (1989) reports about a lecture by Dr. Ing. Srinivasan Sridhar at the Dechema collquium of Feb. 2, 1988 in Frankfurt/M. Said lecture related to the electrodialysis of sodium sulfate, alternatively ammonium malate by using bipolar membranes. At the tests performed a permeate of an ultrafiltration was subjected to a concentration step i.c. an electrodialysis, alternatively a reverse osmosis and subsequently the permeate was supplied to an electrodialysis cell wherein bipolar membranes are used.

Although bipolar membranes are described in the above publications in Chem. Ing. Tech. 59 and 61, herebelow a further description of said membranes is given.

Bipolar membranes are composed of a number of layers of specially formulated, electively permeable membranes. At the interface of the membranes, water molecules are decomposed into hydroxyl ions and hydrogen ions, as indicated in FIG. 1.

Water diffuses out of the surrounding aqueous solution into the membrane interface. Under the influence of electrical direct current, vigorous dissociation of water into $H-$ and $OH-$ ions takes place. Electrodialysis using bipolar membranes makes it possible to extract the acids from salts of organic acids and to concentrate them without introducing foreign anions into the system. The bipolar membrane therefore provides, for example, the possibility of replacing $Na-$ cations and/or $K-$ cations by $H-$ ions in an organic salt. In such a replacement of $Na-$ and/or $K-$ by $H-$ ions, NaOH and/or KOH is frequently produced as a by-product.

In such a cell, there is a bipolar membrane between the anode and an anion-selective monopolar membrane, and furthermore a bipolar membrane between the cathode and a cation-selective monopolar membrane, while the salt inlet and outlet is situated between the said monopolar membranes.

The hydroxyl and hydrogen ions move in opposite directions through the bipolar membranes. At the cation-selective side of the bipolar membranes, the hydrogen ions combine with the electronegative part of dissolved salts to form acids. At the anion-selective side, the hydroxyl ions combine with the electropositive ions to form bases.

Ions migrate through the monopolar membranes to the acidic and basic zones which are situated close to the bipolar membranes.

Figure 2:
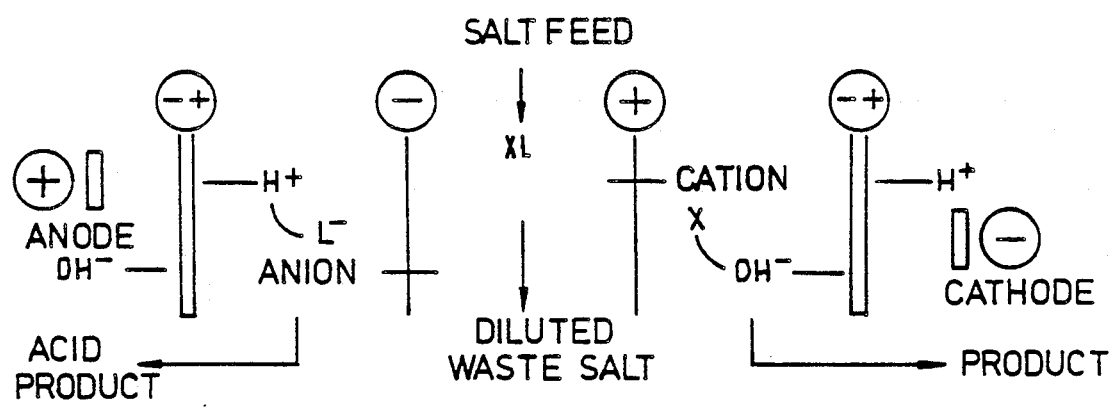

FIG. 2 illustrates the operation of such a three-compartment cell diagrammatically.

Such a three-compartment cell operates, in general, with a potential difference of 1.5-2.5 V/cell and 700 to 1000 $A/m^2$ of membrane surface area.

The thermally stable organic acid obtained has a concentration of approximately 30% by weight.

Additional advantages are furthermore that, during the electrodialysis, the fermentation liquid does not have to be sugarfree, while the base and the residual growth substances can be recycled, as a result of which, in particular, the consumption of hydroxide solution can be very small.

In relation to the reverse osmosis apparatus, it is pointed out that membranes are used therein of the type which is also used for sea water desalination, for example polyamide or cellulose acetate. The pressure in reverse osmosis is 40 to 60 bar.

As observed already at the discussion of Chem. Ing. Tech. 59, 952-954, a disadvantage of the standard media used for this type of fermentations is, that it absolutely required that the media contain any yeast extract and maize culture water if bacteria of the genus Lactobacillus are used.

Surprisingly, it was found now, that in the above process, in case bacilli of the genus Bacillus, particularly *Bacillus coagulans*, are used as fermenting microorganisms instead of the lactobacilli generally used, the growth media used in the fermentive preparation of lactic acid do not need to contain any yeast extract and maize culture water.

The process according to the invention is explained with respect to the process diagram of FIG. 3.

Fermentation medium is continuously introduced into the reaction vessel CSTR through inlet pipe 1. The flow rate is so adjusted, for example, that the product which is fed through pipe 2 to the ultrafiltration apparatus UF contains approximately 6% by weight of salt of the organic acid concerned, which, in the case of potassium lactate, corresponds to 0.66 N lactic acid ions.

In the ultrafiltration apparatus, the reaction medium is split into retentate, which is fed back through pipe 9 into CSTR, and permeate which is passed through pipe 3 into the reverse osmosis apparatus RO in which the pressure which is exerted on the permeate forces the solvent present in the permeate through a semipermeable membrane against the osmotic pressure; as a result of the filtration action, on the one hand, a more concentrated permeate is obtained and, on the other hand, the solvent is obtained. The abovementioned lactic acid ions would be concentrated, for example, to 1.32 N. Then the concentrated salt flows through pipe 4 and $H_2O$ through pipe 5 into the electrodialysis apparatus in which the salt is decomposed into XOH and organic acid. Through pipe 5, $H_2O$ returns to the inlet pipe 1. In the abovementioned case of lactic acid, the concentration would then increase to 4 N; this would be removed through pipe 6. Dilute salt of the organic acid is fed back through pipe 7 into the RO apparatus and XOH is fed back through pipe 8 into CSTR.

If the concentration of the ingredient accumulated in flow 7 becomes too great, a portion of said flow can be passed into the $H_2O$ flow of pipe 5 through pipe 10 in which a shut-off valve is fitted.

EXAMPLE I

The lactic acid production below was carried out with the system shown in FIG. 3.

The CSTR was filled with sterilized medium of the following composition:

6% by weight of glucose,
2.5% by weight of yeast extract,
0.05% by weight of $(NH_4)_2SO_4$,
0.03% by weight of $MgSO_4$,
0.02% by weight of $KH_2PO_4$,
0.02% by weight of $K_2HPO_4$.

The reactor had a working volume of 5 l and was inoculated with 100 ml of Bacillus coagulans culture DSM 2311 which had been precultured on nutrient broth in a shaking flask at 45° C. The fermentation was carried out batchwise for 24 hours under aerobic conditions.

The continuous anaerobic fermentation was then started. The production medium had the following composition:

6.6% by weight of glucose,
0.1% by weight of yeast extract,
0.1% by weight of diammonium phosphate.

The pH was adjusted to 6.0 with ammonium hydroxide. The temperature was adjusted to 50° C.

The ultrafiltration unit used was a biopilot Carbosep PSV 3 R (SFEC) having M6 membranes with a total surface area of 0.1 m². A pressure of 2.2 bar was employed at the inlet and 1.8 bar at the outlet of the module. The RO was a tubular system fitted with organic membranes of type APC 99 (PCI) having a surface area of 0.85 m². A pressure of 60 bar was employed at 35° C.

The electrodialysis stack contained 8 cells (3 compartments) made up of anion-selective, cation-selective and bipolar membranes (Aquatech) having a total surface area of 0.10 m². The voltage used was 25 V at a current density of 100 mA/cm².

The unconverted salt solution from the electrodialysis stack was recycled to the RO. The hydroxide solution produced in the electrodialysis stack was conveyed to the hydroxide vessel and reused for neutralization in the fermenter.

In the steady state the following results were obtained; The lactate concentration in the fermenter was 0.63 N. The volumetric productivity of the fermenter was 60 g/(l.h) at the dilution rate used of 1 h−1. The biomass concentration was approx. 40 g/l (dry weight). The yield for converting glucose into lactic acid was 95%.

In the RO module, the ammonium lactate solution was concentrated to 1.2 N. The product flow from the ED stack was 0.85 l/h and contained 36% lactic acid. The electrical efficiency was 85%.

EXAMPLE II

The experiment of Example I was carried out with a defined medium as product medium having the following composition:

| | |
|---|---|
| glucose | 6.6% by weight |
| diammonium phosphate | 0.2% by weight |
| $KH_2PO_4$ | 0.1% by weight |
| $K_2HPO_4$ | 0.1% by weight |
| $MgSO_4$ | 0.1% by weight |
| biotin | 0.15 μg/l |
| thiamin | 75 μg/l |
| folic acid | 15 μg/l |
| niacin | 1 mg/l |
| arginine | 5 mg/l |
| asparagine | 100 mg/l |
| cysteine | 3 mg/l |
| glutamine | 20 mg/l |
| histidine | 3 mg/l |
| methionine | 10 mg/l |
| proline | 15 mg/l |
| serine | 20 mg/l |

In other respects, the conditions were identical to those of Example I. The results were identical to Example I.

What is claimed is:

1. Process for the fermentative preparation of lactic acid, by allowing a sterilized growth medium to be continuously fermented in a reaction vessel by a culture of bacteria which form lactic acid, keeping the pH of the reaction mixture at 3 to 9 with an aqueous solution of XOH (where X is $NH_4$ or a metal whose hydroxide and whose salt of lactic acid are watersoluble), subjecting the fermented reaction mixture to an ultrafiltration, recycling the retentate to the reaction vessel, and concentrating the permeate by subjecting it in a two-or three compartment cell to an electrodialysis wherein bipolar membranes are used, in which process the salt formed is decomposed into the lactic acid and XOH, where XOH has the above mentioned meaning, characterized in that bacilli of the genus Bacillus are used as fermentative bacteria in a medium in which yeast extract and maize culture water are absent, in the preparation of lactic acid.

2. Process according to claim 1, characterized in that *Bacillus coagulans* is used as fermentative bacterium.

* * * * *

UNITED STATES PATENT AND TRADEMARK OFFICE
CERTIFICATE OF CORRECTION

PATENT NO. : 5,002,881
DATED : March 26, 1991
INVENTOR(S) : Joannes G. M. Van Nispen and Ronald Jonker It is certified that error appears in the above-identified patent and that said Letters Patent is hereby corrected as shown below:

Abstract Line 8 "watersoluble" should read --water-soluble--.

Column 2 Line 23 "H$^-$" should read --H$^+$--.

Column 2 Line 38 "Na$^-$" should read --Na$^+$--.

Column 2 Line 39 "K$^-$" should read --K$^+$--.

Column 2 Line 39 "H$^-$" should read --H$^+$--.

Column 2 Line 40 "Na$^-$ and/or K$^-$ by H$^-$" should read
 --Na$^+$ and/or K$^+$ by H$^+$--.

Column 3 Line 40 "abovementioned" should read --above mentioned--.

Column 3 Line 46 "abovementioned" should read --above mentioned--.

Column 4 Line 1 "5 1" should read --5:1--.

Column 4 Lines 33-34 "obtained;" should read --obtained:--.

Signed and Sealed this

Thirteenth Day of October, 1992

*Attest:*

DOUGLAS B. COMER

*Attesting Officer*   *Acting Commissioner of Patents and Trademarks*